(12) United States Patent
Xu et al.

(10) Patent No.: US 12,616,382 B2
(45) Date of Patent: May 5, 2026

(54) WEARABLE MECHANO-ACOUSTIC SENSOR

(71) Applicant: Wayne State University, Detroit, MI (US)

(72) Inventors: Yong Xu, Troy, MI (US); Zhiguo Zhao, Southfield, MI (US); Xiaoce Feng, Southfield, MI (US); Xiaoyu Chen, Southfield, MI (US)

(73) Assignee: Wayne State University, Detroit, MI (US)

( * ) Notice: Subject to any disclaimer, the term of this patent is extended or adjusted under 35 U.S.C. 154(b) by 644 days.

(21) Appl. No.: 18/095,177

(22) Filed: Jan. 10, 2023

(65) Prior Publication Data

US 2023/0218177 A1 Jul. 13, 2023

Related U.S. Application Data

(60) Provisional application No. 63/298,375, filed on Jan. 11, 2022.

(51) Int. Cl.

| | |
|---|---|
| *A61B 5/0205* | (2006.01) |
| *A61B 5/00* | (2006.01) |
| *A61B 5/11* | (2006.01) |
| *A61B 5/113* | (2006.01) |
| *A61B 7/00* | (2006.01) |

(Continued)

(52) U.S. Cl.
CPC .......... *A61B 5/0205* (2013.01); *A61B 5/1102* (2013.01); *A61B 5/1126* (2013.01); *A61B 5/113* (2013.01); *A61B 5/6823* (2013.01); *A61B 7/003* (2013.01); *A61B 7/02* (2013.01); *G01L 9/18* (2013.01); *A61B 2562/0217* (2017.08);

(Continued)

(58) Field of Classification Search
CPC ...................................................... G01L 9/18
See application file for complete search history.

(56) References Cited

U.S. PATENT DOCUMENTS

| | | | | |
|---|---|---|---|---|
| 3,646,814 A | * | 3/1972 | Christoph | ................. G01L 9/18 |
| | | | | 73/717 |
| 2003/0029719 A1 | * | 2/2003 | Abramovich | ........... G01P 15/12 |
| | | | | 204/252 |

(Continued)

OTHER PUBLICATIONS

Huang et al. "Molecular Electric Transducers as Motion Sensors: A Review." Sensors 2013, 13, 4581-4597. (Year: 2013).*

(Continued)

*Primary Examiner* — Meredith Weare
(74) *Attorney, Agent, or Firm* — Fishman Stewart PLLC

(57) ABSTRACT

A wearable mechano-acoustic sensor for continuous cardio-respiratory monitoring, and methods of making and using the same. The sensor includes a diaphragm with a chamber and a channel connected to the chamber, a plurality of electrodes including at least an anode and a cathode extending into the channel, and a liquid electrolyte solution that fills the chamber and channel. When the diaphragm is attached to a user's chest, mechano-acoustic movement from the chest cause the diaphragm to move, pushing the electrolyte solution across the electrodes. A voltage is applied to the anode and an electrochemical current is determined by the flux from the anode to the cathode by the modulation of the electrolyte solution across the electrodes and cardiorespiratory signals are measured from the electrochemical currents.

20 Claims, 12 Drawing Sheets

(51) Int. Cl.
    *A61B 7/02*         (2006.01)
    *G01L 9/18*         (2006.01)
(52) U.S. Cl.
    CPC ....... *A61B 2562/04* (2013.01); *A61B 2562/12*
             (2013.01); *A61B 2562/168* (2013.01)

(56)           References Cited

U.S. PATENT DOCUMENTS

| | | | | |
|---|---|---|---|---|
| 2005/0257616 A1* | 11/2005 | Kozlov | ................ | G01P 15/006 |
| | | | | 73/514.16 |
| 2012/0299730 A1* | 11/2012 | Rahimi | ................ | A61B 5/1112 |
| | | | | 600/595 |
| 2016/0097641 A1* | 4/2016 | Dai | ........................ | G01C 19/14 |
| | | | | 73/504.12 |
| 2016/0291176 A1* | 10/2016 | Yu | .......................... | G01H 11/06 |
| 2019/0003911 A1* | 1/2019 | Han | ........................ | C08L 79/02 |

OTHER PUBLICATIONS

Agafonov et al. "Electrochemical Seismometers of Linear and Angular Motion." Encyclopedia of Earthquake Engineering, 2015, Springer, Berlin, Heidelberg. (Year: 2015).*

Hu et al., "Physiological Acoustic Sensing Based on Accelerometers: A Survey for Mobile Healthcare," Annals of Biomedical Engineering, Nov. 2014, vol. 2, No. 11, pp. 2264-2277.

Ziaeian et al., "Epidemiology and aetiology of heart failure," Nat Rev Cardiol, Jun. 2016, vol. 13, pp. 368-378.

"Symptoms of Coronavius, Updated May 13, 2020," 2020, Web page <https://www.cdc.gov/coronavirus/2019-ncov/symptoms-testing/symptoms.html>, 3 pages, Sep. 9, 2020, retrieved from Internet Archive Wayback Machine <https://web.archive.org/web/20200909003206/www.cdc.gov/coronavirus/2019-ncov/symptoms-testing/symptoms.html> on May 3, 2023.

Seshadri et al., "Wearable Sensors for COVID-19: A Call to Action to Harness our Digital Infrastructure for Remote Patient Monitoring and Virtual Assessments," Frontiers in Digital Health, Jun. 2020, vol. 2, Article 8, pp. 1-11.

Jeong et al., "Continuous on-body sensing for the COVID-19 pandemic," Sci. Adv., Sep. 2, 2020, vol. 6, pp. 1-4, DOI: 10.1126/sciadv.abd4794.

KunHyuck Lee et al., "Mechano-acoustic sensing of physiological processes and body motions via a soft wireless device placed at the suprasternal notch," Nature Biomedical Engineering, 2020, vol. 4, No. 2, pp. 148-158.

P. Gupta et al., "Precision wearable accelerometer contact microphones for longitudinal monitoring of mechano-acoustic cardiopulmonary signals,". npj Digital Medicine, 2020, vol. 3, doi: 10.1038/s41746-020-0225-7.

Liu et al., "Epidermal mechano-acoustic sensing electronics for cardiovascular diagnostics and human-machine Interfaces," Science Advances, 2016, vol. 2, No. 11, pp. e1601185, doi = 10.1126/sciadv.1601185.

Y. Hu et al., "An Ultra-Sensitive Wearable Accelerometer for Continuous Heart and Lung Sound Monitoring," 34th Annual International Conference of the IEEE Engineering in Medicine and Biology Society, San Diego, CA, USA, 2012, pp. 694-697, doi: 10.1109/EMBC.2012.6346026.

Nayeem et al., "All-nanofiber-based, ultrasensitive, gas-permeable mechanoacoustic sensors for continuous long-term heart monitoring," Proceedings of the National Academy of Sciences of the United States of America, Mar. 31, 2020, vol. 117, No. 13, pp. 7063-7070, https://doi.org/10.1073/pnas.1920911117.

Deng et al., "A MEMS Based Electrochemical Vibration Sensor for Seismic Motion Monitoring," in Journal of Microelectromechanical Systems, Feb. 2014, vol. 23, No. 1, pp. 92-99, doi: 10.1109/JMEMS.2013.2292833.

Agafonov et al., "Convective Current in a Four-Electrode Electrochemical Cell at Various Boundary Conditions at Anodes," Russ J Electrochem, 2005, vol. 41, pp. 880-884. https://doi.org/10.1007/s11175-005-0148-2.

Newson et al., "The Kinetics of the Iodine Redox Process at Platinum Electrodes," Journal of The Electrochemical Society, 1961, vol. 108, No. 7, pp. 699, :/dx.doi.org/10.1149/1.2428192.

Huang et al., "A micro seismometer based on molecular electronic transducer technology for planetary exploration," Applied Physics Letters, May 2013, vol. 102, iss. 19, 193512, https://doi.org/10.1063/1.406983.

Website excerpt from http://www.smooth-on.com/, "EcoflexTM Series, Super-Soft, Addition Cure Silicone Rubbers", 2 pages (retrieved on Jan. 11, 2023).

X. Fu et al., "A novel sound sensor and its package used in lung sound diagnosis," 2014 IEEE 64th Electronic Components and Technology Conference (ECTC), Orlando, FL, USA, 2014, pp. 1189-1191, doi: 10.1109/ECTC.2014.6897441.

Gorlov et al., "Ionic liquid electrolytes for dye-sensitized solar cells," Dalton Trans., 2008, issue 20, pp. 2655-2666 (publisher: The Royal Society of Chemistry).

\* cited by examiner 610   620   630   500 RPM   0.5mm   640   650   660   28mm   670

*1102* *1104* *1102* *1104* *1102* *1104* *1102* *1104* *1102* *1104*

*1106*

*1100*

Voltage (mV)

Time (sec)

Voltage (mV)

Time (sec)

*1110* *1112* *1116* *1114*

1

WEARABLE MECHANO-ACOUSTIC SENSOR

CROSS-REFERENCE TO RELATED APPLICATIONS

This application claims priority to U.S. Provisional Application 63/298,375, filed on Jan. 11, 2022, the contents of which is incorporated herein by reference in its entirety.

TECHNICAL FIELD

This disclosure relates generally to a wearable mechano-acoustic sensor for monitoring cardiorespiratory signals.

BACKGROUND

Heart and respiration activities offer physiological and pathological information through mechano-acoustic signals. Continuous monitoring of these signals may significantly improve the diagnosis and management of many cardiovascular and respiratory diseases. One example is heart failure (HF), which impacts over 37.7 million people globally. HF patients may have a very high rate of re-hospitalization, which may account for a large percentage of the total medical cost. It is envisioned that self-management of HF using wearable mechano-acoustic sensors may effectively decrease the re-hospitalization rate, improve the quality of life, and reduce mortality.

In addition, common symptoms of respiratory disease and pneumonia like COVID-19 may include fever, cough, sore throat, and body aches, all of which may lead to shortness of breath. Abnormal heart and respiration signals may become a sign of infection for pre-clinical diagnosis. Symptoms in the early stage of infection may be subtle and asymptomatic. Therefore, wearable devices that are capable of accurate detection of subtle respiratory and cardiovascular variation, may be of great interest especially in the COVID-19 pandemic.

Many wearable sensors have already been developed for recording heart or respiratory sounds continuously using custom-designed or off-the-shelf accelerometers. As the technology of flexible and stretchable electronics advances, wearable acoustic sensors based on polymer materials are known.

However, there is a need for improved wearable sensors. Some more commonly available and used wearable devices offer limited information. For example, many wearable heart rate monitors utilize photoplethysmography, measuring heart rate by shining a green light through the skin, which may work better on lighter rather than darker skin. More accurate methods may be harder to track using a wearable device continuously.

Thus, although the current methods of monitoring cardiorespiratory signals have been used to make diagnosis and treatment decisions, there is a need for having an ultra-high sensitive sensor for continuous cardiorespiratory monitoring.

BRIEF DESCRIPTION

According to the disclosure, a sensor for monitoring cardiorespiratory signals includes a diaphragm with a chamber and a channel connected to the chamber. The sensor includes a plurality of electrodes extending into the channel. The plurality of electrodes includes at least a first anode and a first cathode. The sensor includes a liquid electrolyte solution that fills the chamber and flows into the channel, surrounding the plurality of electrodes. When a voltage is applied to the first anode, an electrochemical current is detectable as an ionic flux from the first anode to the first cathode. The electrochemical current is varied or modulated when the liquid electrolyte solution moves across the plurality of electrodes from the mechano-acoustic movement from a chest.

Also according to the disclosure, a method of using a sensor to monitor cardiorespiratory signals includes placing a sensor having a chamber and a channel on a chest of a user, applying a DC voltage to the plurality of electrodes, and detecting a mechano-acoustic signal by measuring two reversable electrochemical currents between the plurality of electrodes that are modulated by passing an electrolyte solution from the chamber across the plurality of electrodes as a result of mechano-acoustic movement of the chest.

According to the disclosure, a method of manufacturing a sensor to monitor cardiorespiratory signals includes building a chamber from a silicone rubber, spin-coating a diaphragm from the silicone rubber, attaching the chamber to the diaphragm, inserting electrodes into the channel, filling the chamber with a liquid electrolyte solution; and sealing the chamber.

Also according to the disclosure, a system for monitoring cardiorespiratory signals includes a diaphragm including a chamber and a channel connected to the chamber, the diaphragm attached to a chest of a user and flexible to move with the chest. The system includes a plurality of electrodes including an anode and a cathode, the plurality of electrodes extending into the channel. The system includes a liquid electrolyte solution filling the chamber and the channel, the liquid electrolyte solution able to flow across the plurality of electrodes as mechano-acoustic movement of the chest moves the diaphragm. The system includes a voltage source configured to apply a voltage to the anode such that a reversable electrochemical current is detectable as an ionic flux from the anode to the cathode when the liquid electrolyte solution modulates across the plurality of electrodes. The system includes a controller for detecting the electrochemical currents and measuring cardiorespiratory signals from the electrochemical currents.

DETAILED DESCRIPTION

Figure 1:
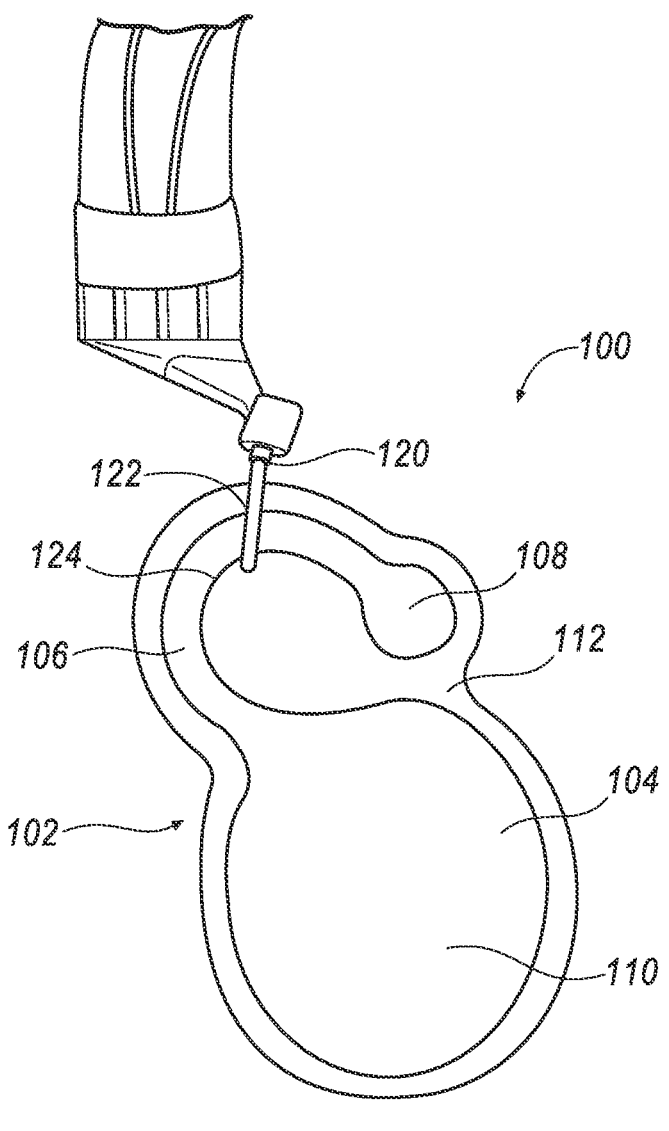
FIG. 1 illustrates a wearable mechano-acoustic sensor on the chest of a user.

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the disclosure to the precise form and configuration shown in the drawings and disclosed in the following detailed description.

Disclosed is a device for monitoring cardiorespiratory signals, including a flexible diaphragm with a circular chamber, a narrow channel connected to the chamber, and a set of electrodes extending into the channel. The chamber and the channel are filled with a liquid electrolyte solution, and when the device is attached to the chest of a user, a mechano-acoustic movement from the chest causes the flexible diaphragm to move the liquid electrolyte solution into the channel such that the movement is electrochemically detected by the electrodes and cardiorespiratory signals are measured.

In this disclosure, a device and methodology include a wearable mechano-acoustic sensor for continuous cardiorespiratory monitoring. The sensing mechanism is based on reversible iodide/triiodide $$(I^-/I_3^-)$$

electrochemical redox reaction on micro-fabricated platinum electrodes, enabling an ultra-high sensitivity on the detection of mechano-acoustic signals of cardiorespiratory system. A silicone rubber is adopted as the material of the sensor body due to its excellent stretchability, robustness, and skin-compatibility. Detection of heart sounds, lung sounds, as well as respiration rates are obtained by its use.

Figure 2:
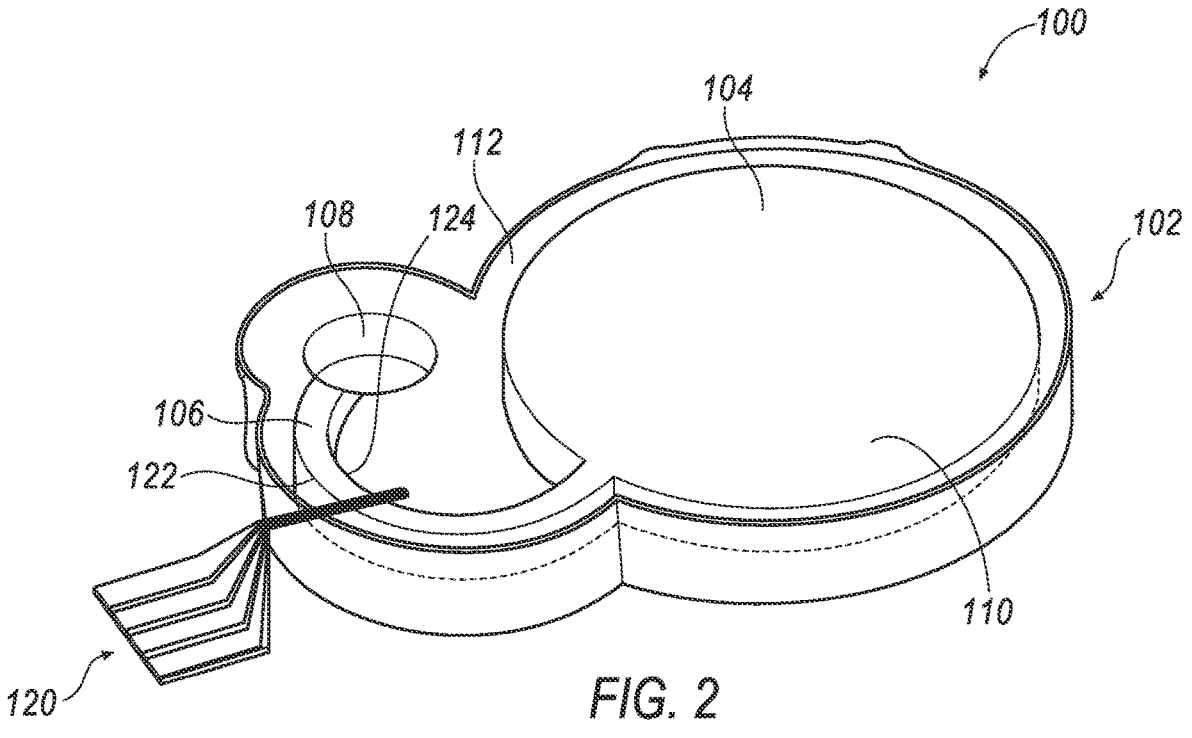
FIG. 2 illustrates a 3D schematic of a wearable mechano-acoustic sensor.
Figure 3:
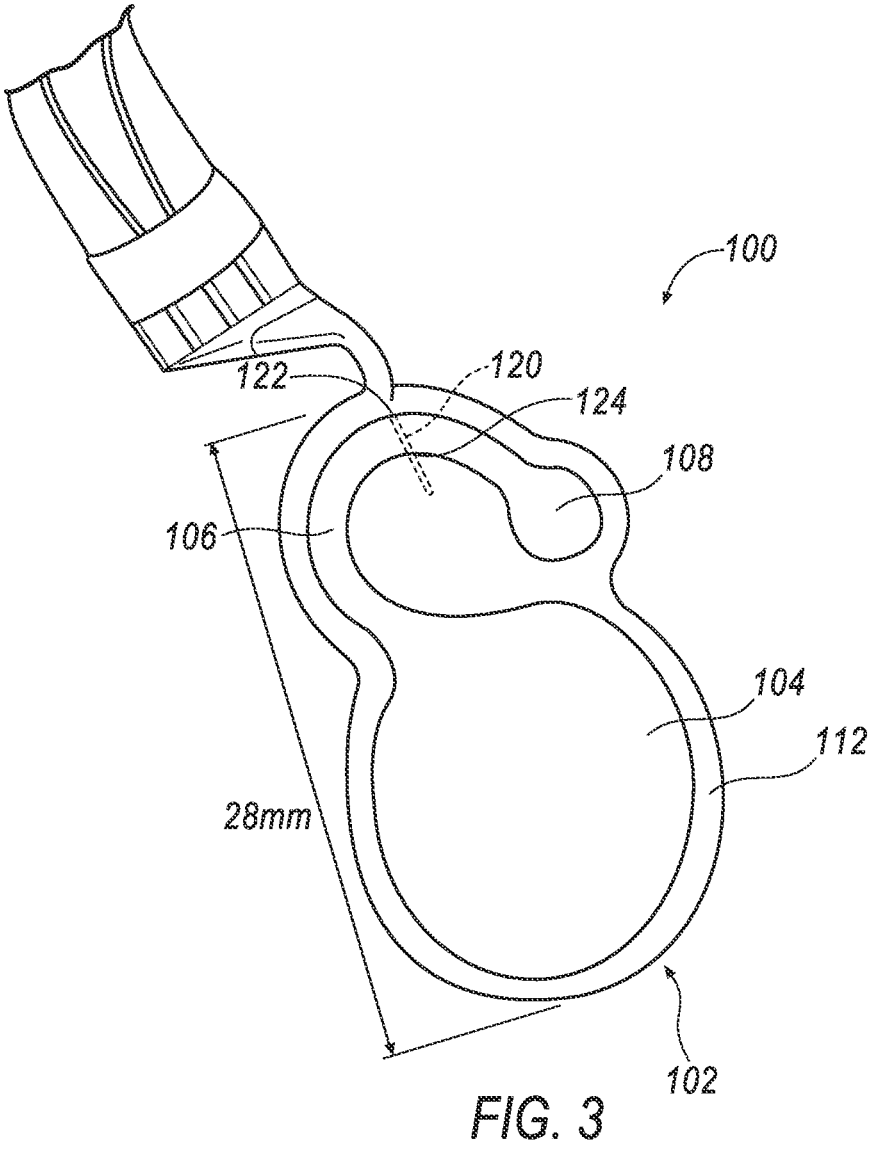
FIG. 3 illustrates an exemplary wearable mechano-acoustic sensor.

Referring to FIGS. 1-3, a wearable mechano-acoustic sensor 100 is provided. Sensor 100 includes a sensor body 102. Sensor body 102 is a flexible silicone rubber that is soft, strong, and stretchy, used due to its properties which make it a wearable material for its flexibility and comfortability on a user. Sensor body 102 includes a chamber 104 for containing an electrolyte solution 110. In one example, chamber 104 is circular as illustrated, however additional shapes may be used such as a square or oval. Chamber 104 includes a narrow channel 106 connected to chamber 104 such that electrolyte solution 110 in chamber 104 flows freely between chamber 104 and channel 106. Channel 106 in one example extends from a top region of chamber 104 in a semi-circle shape for optimal performance, as well as optimal packaging and user experience. However, various other shapes and sizes of channel 106 may be used. Also, sensor 100 may not include channel 106, and instead may consist solely of chamber 104. However, utilizing channel 106 increases accuracy of sensor 100, creating a location of localized higher flow amplitude of electrolyte and thus higher sensitivity in signal detection. Therefore, while cardiorespiratory signals may be measured in chamber 104, measurement of the signals in channel 106 will provide more accurate and sensitive data.

At a terminal end of channel 106, opposite chamber 104, channel 106 is connected to a cavity 108 that, in this example, is circular. Chamber 104 and channel 106 are filled with electrolyte solution 110. Cavity 108 is void of electrolyte solution 110 and is used as a volume to compensate for volumetric changes during operation and to prevent pressure buildup within channel 106, allowing electrolyte solution 110 to move within chamber 104 and channel 106. Thus, during operation and as electrolyte solution 110 moves, expands, and/or contracts then a volume of gas within cavity 108 accommodates such operation.

FIG. 3 shows an exemplary 28 mm dimension from one end of sensor body 102 to the other end and beyond narrow channel 106. It is contemplated that other dimensions may also be used and that the disclosure is not so limited.

Figure 4:
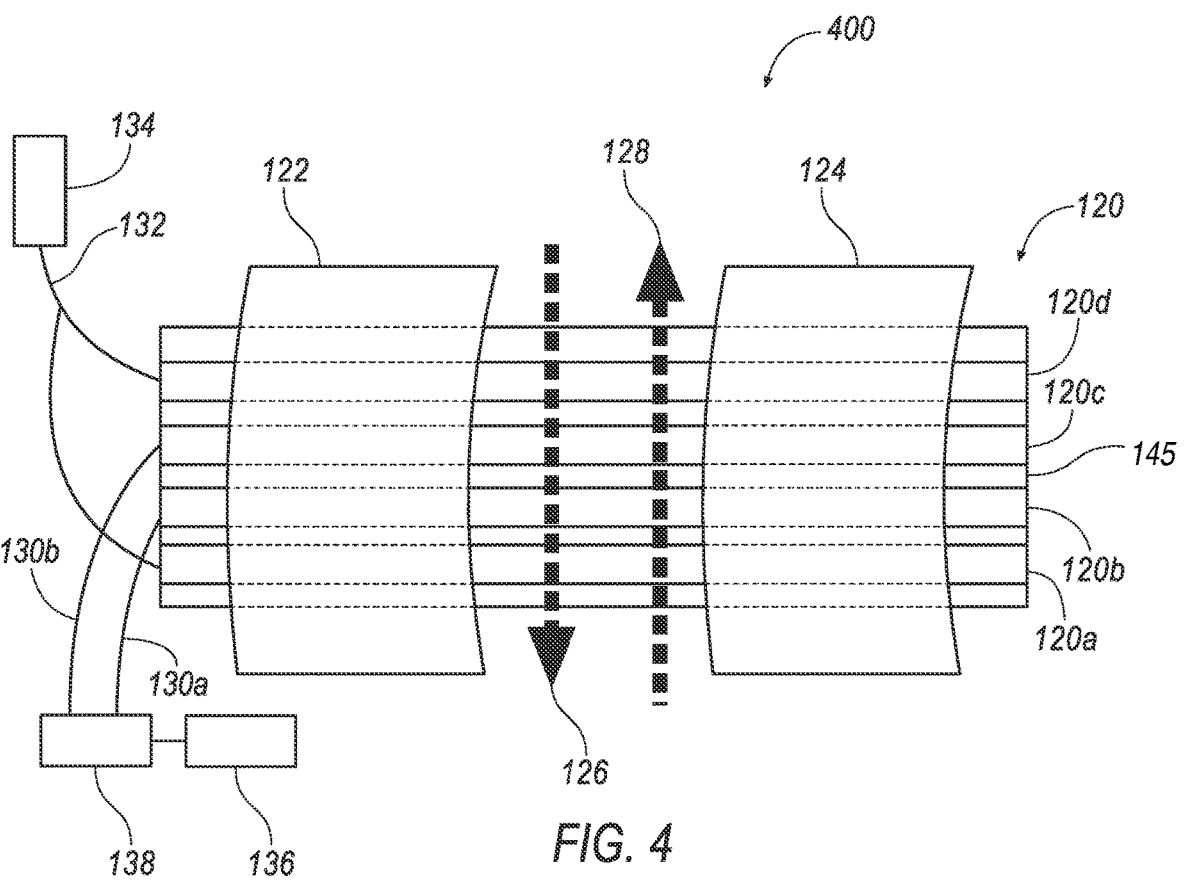
FIG. 4 illustrates an exemplary electrode configuration.

As illustrated in FIG. 4, a system 400 includes sensor 100 as described above including a plurality of electrodes 120 positioned in channel 106 such that electrodes 120 are inserted through and extend through a first side wall 122 and a second side wall 124 of channel 106. Electrodes 120 are positioned to pass through channel 106 and are surrounded by electrolyte solution 110 in channel 106. Plurality of electrodes 120 include four electrodes 120A, 120B, 120C, 120D, but alternate arrangements may include more or less electrodes 120. In other examples, various other numbers of electrodes may be used, with at least one anode 132 and one cathode 130. As illustrated, plurality of electrodes 120 includes two anode-cathode pairs arranged in an anode-cathode-cathode-anode configuration, with electrodes 120A, 120D as the anode 132 and electrodes 120B, 120C the cathode 130. Electrodes 120A, 120D include anode 132 wire out to voltage source. Electrodes 120B, 120C each include cathode 130A, 130B wires out. In other non-limiting examples, sensor 100 may include three electrodes 120 with a cathode-anode-cathode configuration or may include two electrodes 120 with an anode-cathode configuration. In one embodiment, electrodes 120 are platinum and 200 nm thick and 100 μm wide. In one example, electrodes 120 are fabricated on a silicon wafer 145 covered with silicone dioxide. In one example, the distance between electrodes 120A, 120B, 120C, 120D of the plurality of electrodes 120 are 10 μm. In other examples, various other electrode substrates may be utilized including flexible polyimide electrodes to improve the reliability of the sensor.

Figure 5:
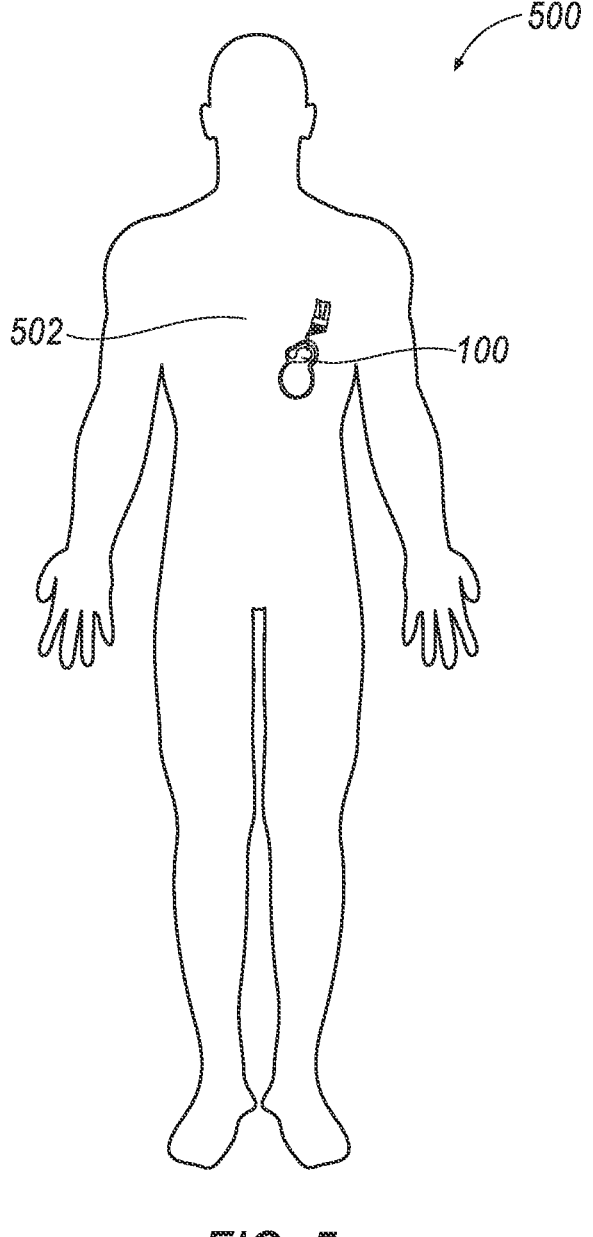
FIG. 5 illustrates an exemplary placement of a wearable mechano-acoustic sensor positioned on the chest of a user.

Referring to FIG. 5, a user 500 includes sensor 100 attached to their chest 502. Typically, user 500 attaches sensor 100 to the left anterior intercostal space above the level of the third rib. The ultra-high sensitivity nature of sensor 100 allows user 500 to place sensor 100 in locations elsewhere on the chest 502 other than the left chest near the heart, where illustrated, while still acquiring good heart sounds, as opposed to conventional devices which may require positioning on the left side of the chest. Sensor 100 is in contact with the skin of user 500 for optimal measurement of cardiovascular symptoms. Sensor 100 may be made of a flexible silicone rubber that is soft, strong, and stretchy. Silicone rubber is a wearable material for its flexibility and comfortability on users. In one example, silicone rubber is skin safe, making it a desirable material for a wearable device, however a different skin safe silicone rubber may also be used.

Electrolyte solution 110 within chamber 104 and channel 106 is an ionic solution. In one embodiment, electrolyte solution 110 may be an electrolyte containing iodide/triiodide (I−/I3−) redox couple, which in other applications has been used to construct high performance seismometers. The ultra-high sensitivity of the solution 110 enables the detection of subtle mechano-acoustic signals. Referring again to FIGS. 1-4, a flexible diaphragm 112 of sensor body 102 surrounds chamber 104. Diaphragm 112 is attached to chest 502 of user 500. Diaphragm 112 is flexible, made of a silicone rubber such that diaphragm 112 may move with micro-movements of chest 502 due to mechano-acoustic signals such as heartbeats and breathing. Diaphragm 112 converts external mechano-acoustic signals to motions of electrolyte solution 110 in channel 106 as diaphragm contracts and restricts with chest 502 movement. The mechano-acoustic signals are then detected electrochemically by electrodes 120. For example, small motions in user 500 chest 502 that arise from breathing and heartbeat cause flexible diaphragm 112 to move electrolyte solution 110 from chamber 104 into narrow channel 106 of sensor 100. Once in channel 106, such motion proximate electrodes 120 is detected electrochemically in the solution, as well as the frequency of the mechano-acoustic signals.

Referring again to FIG. 4, anode 132 is connected to a voltage source 134 to apply a voltage to electrodes 120A, 120D. Cathodes 130A, 130B are connected to a trans-impedance amplifier 138 to convert the current signal to voltage and then to a controller 136 for recording and processing the output signals. In operation, when a DC voltage (e.g., 0.5 V) is applied to an anode 132 of the electrodes 120, while the cathode 130 is connected to zero potential, the following reversible reaction occurs:

Cathode:

$$I_3^- + 2e^- \to 3I^-$$

Anode:

$$3I^- - 2e^- \to I_3^-$$

Anode 132 (120A, 120D) and cathode 130 (120B, 120C) serve as the source and sink of triiodide ions, respectively. The electrochemical current is determined by an ionic flux, for example a triiodide flux, from anode 132 to cathode 130, which is modulated by the motion of electrolyte in channel moving past electrodes 120 in directions 126, 128. Therefore, the external mechano-acoustic signal is detected by measuring the two electrochemical currents of the two electrode pairs. Cathodes 130 are connected to a trans-impedance 138 to convert electrochemical current signals to voltages and then to a controller 136 such as a data acquisition board for measuring the electrochemical currents and detecting external mechano-acoustic signals from breathing and heartbeat. Also, controller 136 outputs mechano-acoustic signals for reading cardiorespiratory information.

In operation, as a user's heart beats and/or breathes, mechano-acoustic movement of user's chest causes diaphragm 112 to move with chest. As diaphragm 112 moves, electrolyte solution 110 in chamber 104 and channel 106 moves, flowing in directions 126, 128 across plurality of electrodes 120. Thus, movement of chest from heartbeats and/or breathing causes movement of electrolyte solution 110 in first direction 128 and second direction 126. For example, as a heat beats, micro-motion of chest causes electrolyte solution 110 to move in a first direction 128 away from chamber 104 and towards cavity 108, moving past plurality of electrodes 120. As micro-motion of chest retracts, electrolyte solution 110 may move in a second, opposite direction 126 back towards chamber 104, moving past plurality of electrodes 120.

When a DC voltage is applied to anode 132 (120A, 120D) by voltage source 134, reversable electrochemical redox reaction occurs between the anodes 132 and cathodes 130, allowing electrochemical currents to be determined by the ionic flux from anode 132 to cathode 130. In one example, reaction is a reversible iodide/triiodide $$\left( I^-/I_3^- \right)$$

electrochemical redox reaction. Trans-impedance amplifier 138 converts the electrochemical current signals to voltages. Controller 136 records and processes the voltage output signals and detects external mechano-acoustic signals and outputs a readable form of user's cardiorespiratory information based on electrochemical currents.

In one example, a liquid electrolyte contains iodide/triiodide $$\left( I^-/I_3^- \right)$$

redox couple. However, alternative electrolytes may include an electrolyte containing Co (II/III) redox couple, or a redox with an exact opposite redox reaction at the anode and cathode may be utilized. An iodide/triiodide $$\left( I^-/I_3^- \right)$$

redox couple or similar alternative electrolyte with an exact opposite redox reaction at the electrodes should be used so that there is no net charge in the electrolyte when a current passes through the solution. In order to obtain a sufficiently sensitive sensor, the bias current needs to be large, such that it is proportional to the redox couple concentrations in the electrolyte. In the illustrated embodiment, the bias current is proportional to the iodide/triiodide concentrations in the electrolyte. Therefore, high concentrations of potassium iodide and iodine are used, such as a liquid solution containing approximately 4.78 mol/l potassium iodide (KI) and 0.04 mol/l iodine fills the circular chamber and narrow channel in the example. The electrolyte should be sufficient to dissolve enough KI and iodide so that the concentrations of iodide and triiodide ions are sufficient, leading to the sufficient bias current and sensitivity. An ionic liquid may be used to replace water, but potential drawbacks are lower ion concentration and larger viscosity.

In considering the electrolyte solution, additional properties of the solution are considered for optimal performance. For example, a solution that is too viscous may not provide enough frequency or sensitivity as the solution is slowed in movement due to internal friction. Solubility of iodine is important in the formation of $$I_3^-.$$

Additionally, to ensure long-term storage of the sensor, an ionic liquid electrolyte with low or almost zero vapor pressure may be included in the solution. Additional carrier liquids or mixtures may be considered based on use. For example, antifreeze such as ethylene glycol or propylene glycol may be added to lower the freeze point of the electrolyte, to allow for outside storage, shipping in an aircraft, and the like.

Figure 6:
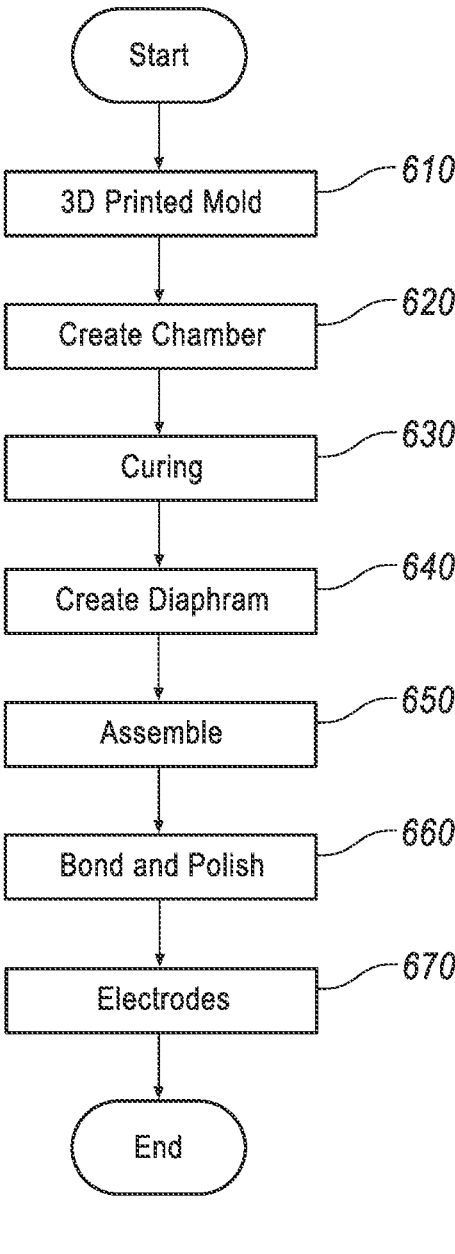
FIG. 6 illustrates a fabrication process of a wearable mechano-acoustic sensor.
Figure 7:
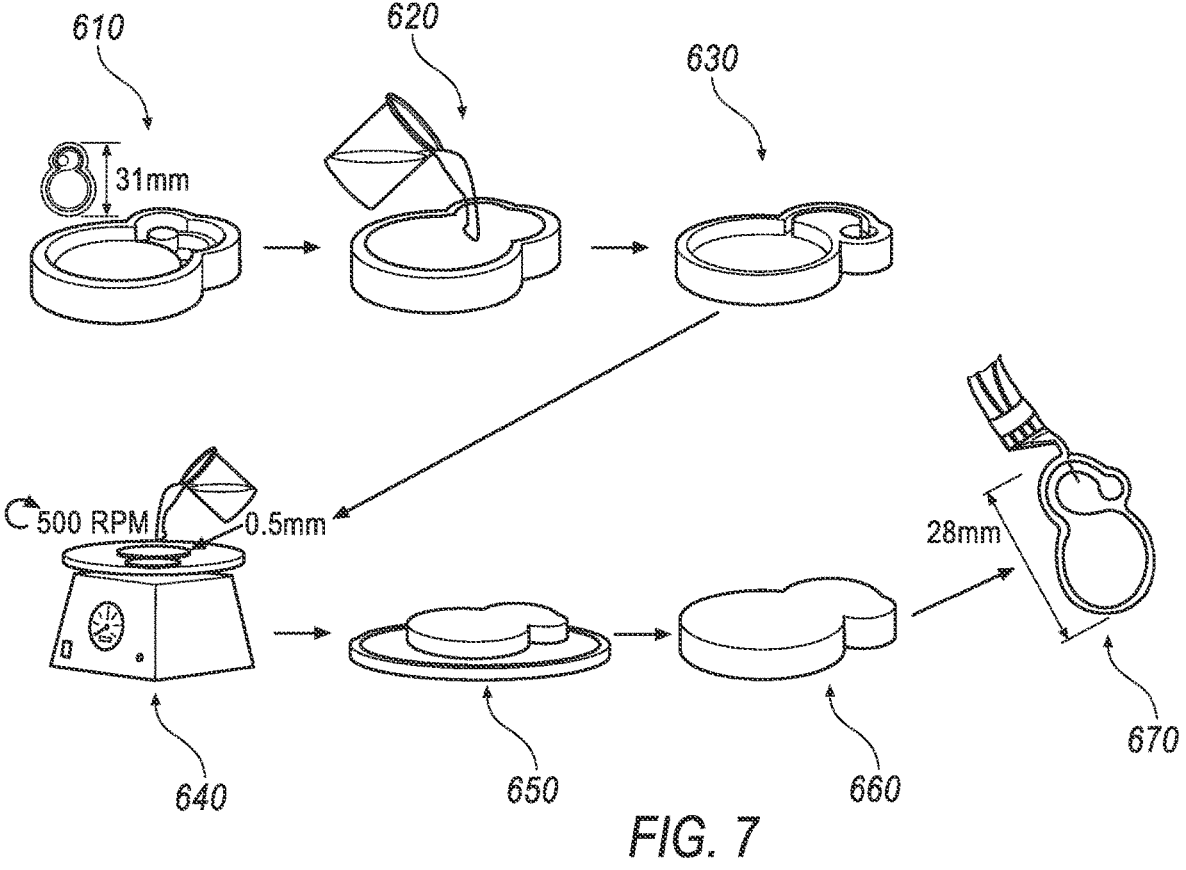
FIG. 7 illustrates a fabrication process of a wearable mechano-acoustic sensor.

Referring to FIGS. 6 and 7, a method 600 of fabricating and assembling sensor 100 is illustrated. Method 600 begins for assembling sensor 100. At 610, a mold for chamber 104 may be built with ECO Acrylonitrile butadiene styrene (ECO-ABS) by 3D printing. Additional 3D printing materials and thermoplastic polymers may also be used for creating mold. At 620, a silicone rubber mixture is poured into the mold and then followed by a degassing process in a vacuum chamber for at least 15 minutes until bubbles are pumped out. At 630, chamber 104 is ready after the silicone rubber is completely cured. The illustrated dimensions in FIG. 7 are shown for exemplary purposes and it is contemplated that other dimensions may be used as well.

At 640, to make diaphragm 112 to be sufficiently thin, silicone rubber mixture is spin-coated on an acrylic sheet around 500 RPM for 10 seconds, resulting in about 500 μm film. Prior to spin-coating, a degassing process is carried out for better film quality. At 650, the previously made chamber body 104 is gently put on the newly spin-coated silicone rubber film upside down, allowing the liquid rubber mixture to evenly contact the top surface of chamber body. At 660 and after silicone rubber is completely cured, chamber body 104 and diaphragm 112 are bonded together. At 670, electrodes 120 are inserted into channel 106 and sealed with marine epoxy. Finally, chamber 104, including channel 106, is filled with a liquid electrolyte solution 110. After method 600 steps above, sensor 100 is assembled and ready for use.

Figure 8A:
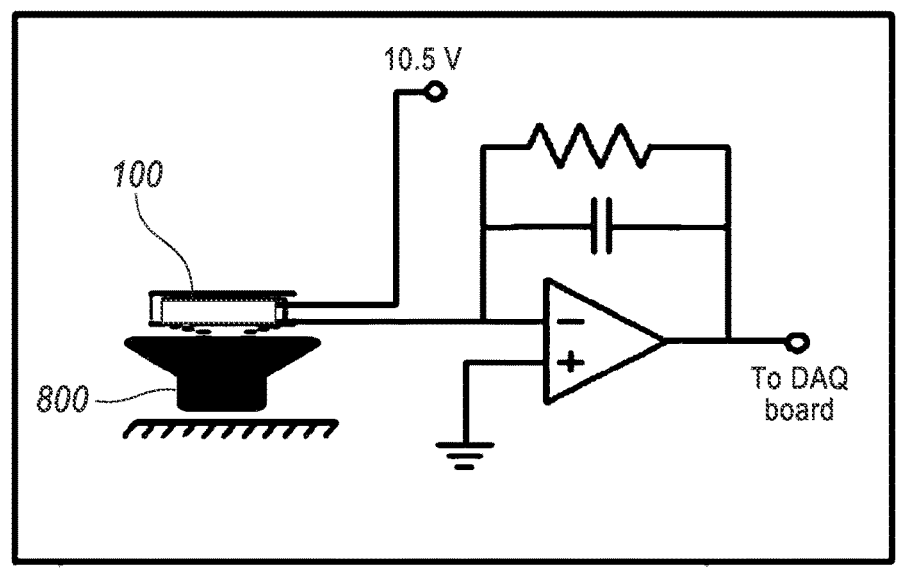
FIGS. 8A and 8B illustrate a characterization setup of a wearable mechano-acoustic sensor and an exemplary frequency response of a wearable mechano-acoustic sensor.

The characterization of sensor 100 may be performed using the setup illustrated in FIG. 8A. Sensor 100 is placed on a speaker 800. 5 mm thick silicone rubber is filled between speaker 800 and diaphragm 112 to emulate human skin between a heart and/or lungs and diaphragm 112 on a chest 502. A 0.5 V DC voltage is applied to electrodes 120A, 120D, anodes 132, and two trans-impedance amplifiers, each with a 10 kΩ feedback resistor and an 8.5 nF feedback capacitor are connected to electrodes 120B, 120C, cathodes 130, to convert the current signal to voltage.

The two output signals are recorded by a data acquisition board such as a National Instruments USB-6002 with a sampling rate of 4096 Hz when the speaker is driven by an AC voltage of different frequencies. Then the differential signals are calculated and processed. An accelerometer is placed on the surface of the silicone layer to measure the acceleration.

Figure 8B:
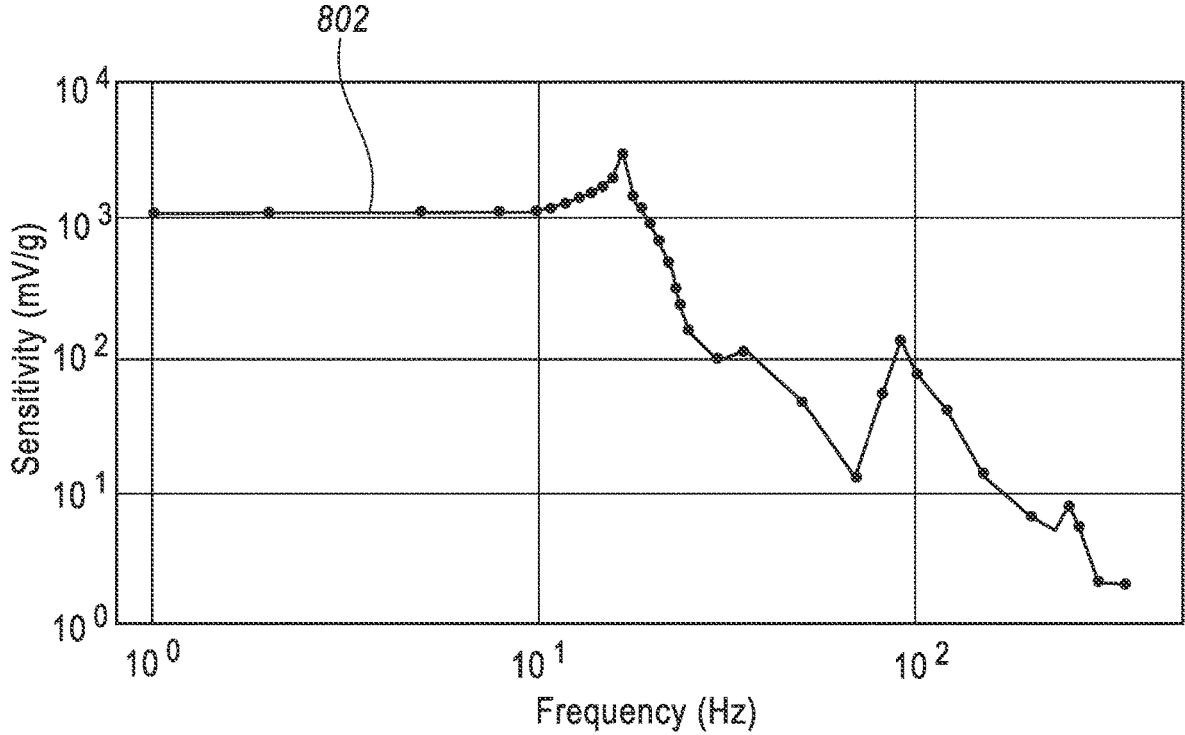
Figure 9A:
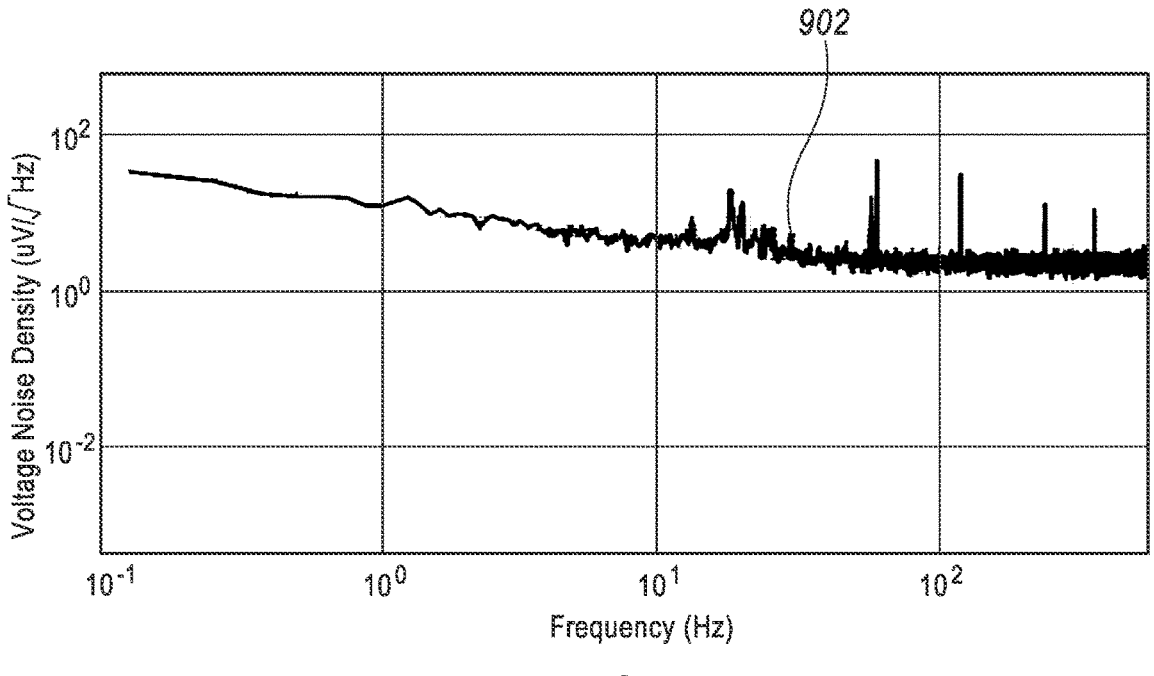
FIGS. 9A and 9B illustrate differential voltage in the time domain and exemplary noise spectrum of the differential voltage.
Figure 9B:
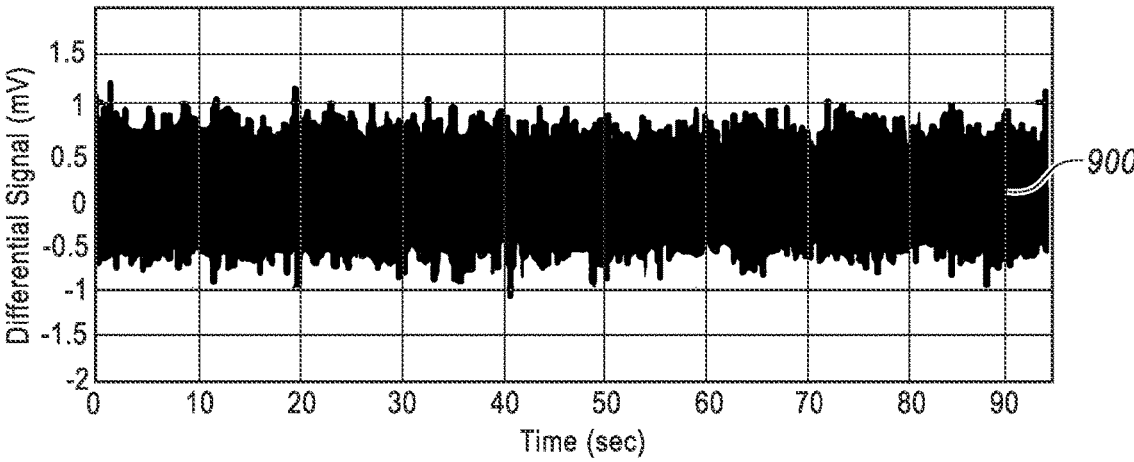

The sensitivity of the device as a function of frequency 802 is illustrated in FIG. 8B. The resonant frequency of the device is 17 Hz and the sensitivity below 10 Hz is around 1100 mV/g. The noise spectrum of the differential signal 900 is illustrated in FIG. 9B. The standard deviation of the time domain noise output is 0.21 mV over a bandwidth from 20 Hz to 500 Hz. Based on the sensitivity data 802 in FIG. 8B and noise data 902 in FIG. 9A, the minimum detectable acceleration is 4.5 μg/√Hz at 10 Hz, which is better than most MEMS accelerometers. Thus, the power spectral density at 10 Hz is 4.5 μg/√Hz, suggesting the sensitivity and ability to measure the mechano-acoustic signals is better than most MEMS accelerometers, requiring a lower minimum noise to detect the signals.

Figure 10:
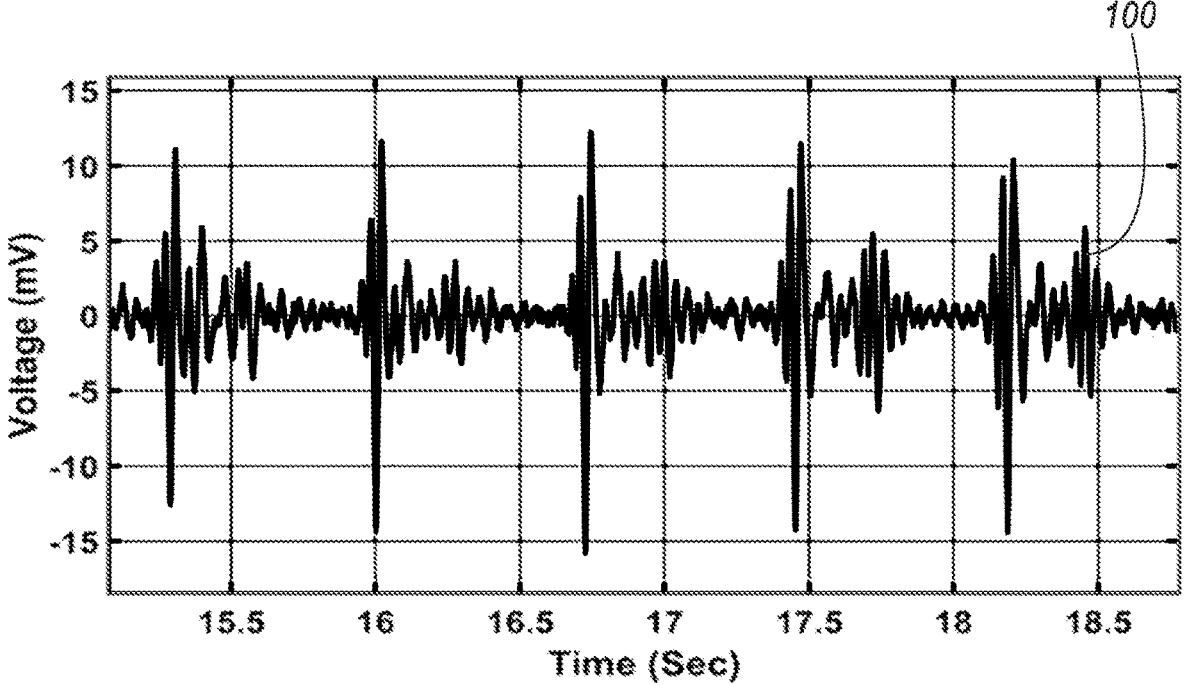
FIG. 10 illustrates an exemplary sample waveform of heart sounds.

Tests for the detection of heart sounds, lung sounds, as well as the respiration rates are illustrated. FIG. 10 illustrates a sample of heart sounds waveform 1000 obtained by sensor 100. A filter with a bandwidth from 20 Hz to 300 Hz was applied to extract the heart sounds. The waveform 1000 of heart sounds can be observed and exhibits consistency. The heart sound signal illustrated in FIG. 10 was recorded while the sensor was attached to the right chest. Due to the sufficient sensitivity of sensor 100, a sufficient signal-to-noise ratio was still achieved (higher than 6:1) even when sensor 100 is not placed directly over heart.

Figures 11A, 11B:
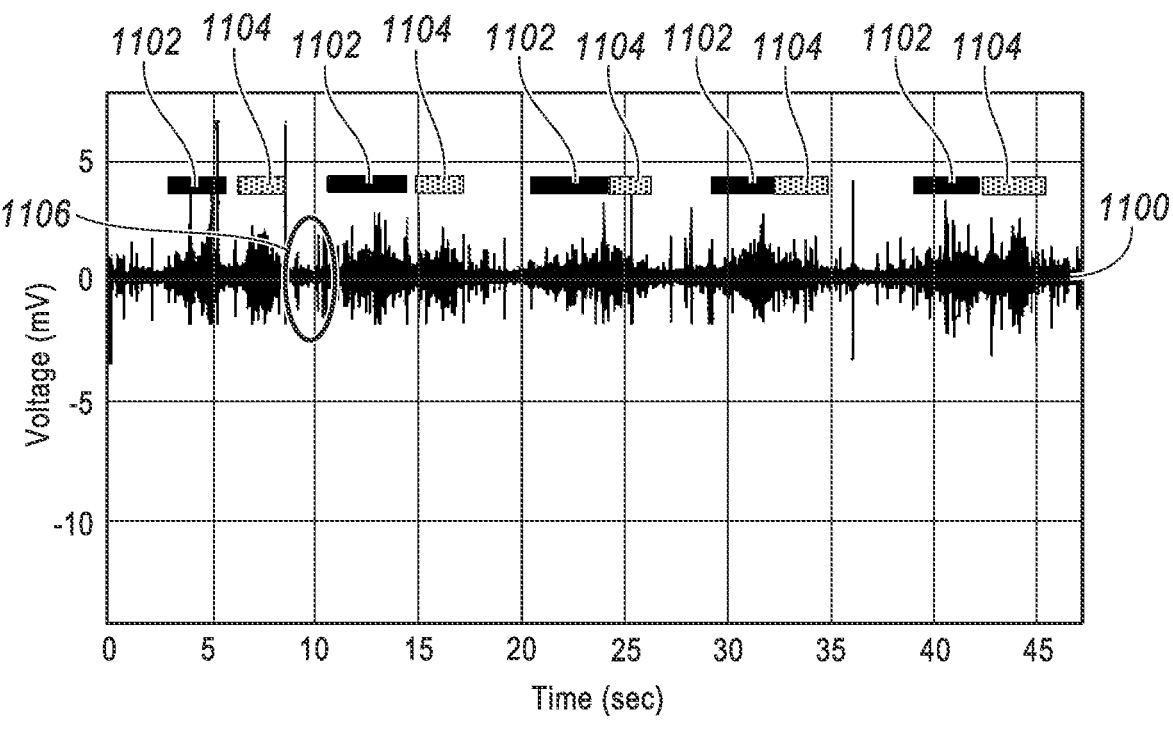
FIGS. 11A and 11B illustrate exemplary lung sounds of regular breathing cycles and lung sounds of an inhalation-hold-exhalation cycle.

The results of lung sound detection are illustrated in FIGS. 11A and 11B. A filter with bandwidth from 75 Hz to 500 Hz was applied. FIG. 11A illustrates the lung sounds 1100 of five consecutive regular breathing cycles of a user. The inhalation periods are marked with bars 1102, and bars 1104 mark the exhalation periods. During the first and the second breathing cycle, the user paused breathing for 1 second between the inhalation and exhalation, and this action was faithfully reflected on the waveform 1100 at period 1106. FIG. 11B illustrates the lung sound waveform 1110 of one long breathing cycle consisting of an inhalation period 1112, a twelve second breath-holding period 1116, and an exhalation period 1114. The borders of these periods can be located on the waveform.

Figure 12:
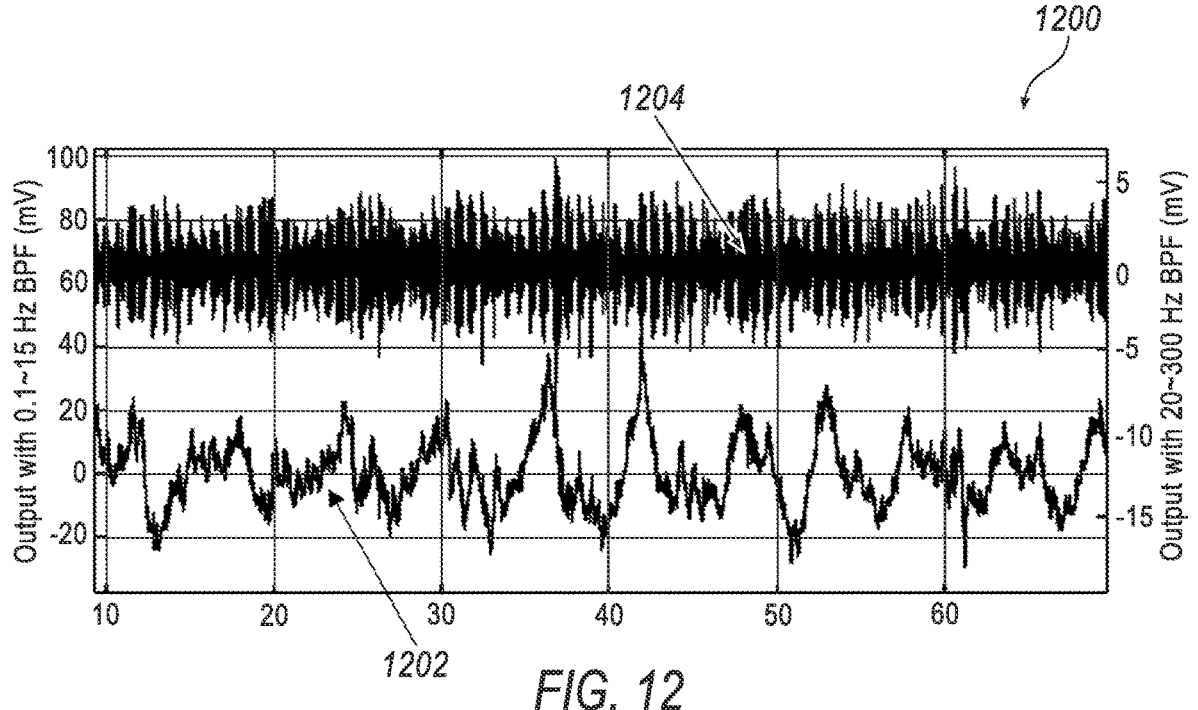
FIG. 12 illustrates exemplary respiration signals.

Apart from the heart sounds and lung sounds detection, the device is also capable of detecting respiration rates, as illustrated in FIG. 12. The respiration rate 1200 can be detected by two different mechanisms.

First, due to its stretchability, sensor 100 is able to deform with the chest when it contracts and expands during respiration, and functions as a strain sensor. This sensing modality is illustrated in the bottom waveform 1202 of FIG. 12 which represents the low frequency component of the signal (filtered with a 0.1 Hz to 15 Hz bandpass filter). Ten respiration cycles are observed from the low-frequency variation of the signal.

Second, the volume change of the chest modulates the amplitude of heart sounds signals. Therefore, the respiration rate may also be detected from filtered heart sounds signal, as shown in the top waveform 1204 of FIG. 12, in which a 20 Hz to 300 Hz bandpass filter is applied. The cyclic change in the heart sound amplitude corresponds to the low-frequency variation of the raw data. Therefore, the respiration rate can be obtained from both signals.

Thus, the disclosed electrochemical wearable sensor is disclosed with its capability to detect cardiorespiratory signals demonstrated. The electrochemical method based on $$\left(I^-/I_3^-\right)$$

redox couple proves to be a sensitive transduction mechanism, enabling the wearable detection of heart sounds, respiration rates and even the much weaker lung sounds. Furthermore, the low cost, robustness, flexibility and stretchability are all desirable merits for wearable health monitoring.

According to the disclosure, a sensor for monitoring cardiorespiratory signals includes a diaphragm with a chamber and a channel connected to the chamber. The sensor includes a plurality of electrodes extending into the channel. The plurality of electrodes includes at least a first anode and a first cathode. The sensor includes a liquid electrolyte solution that fills the chamber and flows into the channel, surrounding the plurality of electrodes. When a voltage is applied to the first anode, an electrochemical current is detectable as an ionic flux from the first anode to the first cathode which is modulated when the liquid electrolyte solution moves across the plurality of electrodes from the mechano-acoustic movement from a chest.

Also according to the disclosure, a method of using a sensor to monitor cardiorespiratory signals includes placing a sensor having a chamber and a channel on a chest of a user, applying a DC voltage to the plurality of electrodes, and detecting a mechano-acoustic signal by measuring two reversable electrochemical currents between the plurality of electrodes that are modulated by passing an electrolyte solution from the chamber across the plurality of electrodes as a result of mechano-acoustic movement of the chest.

According to the disclosure, a method of manufacturing a sensor to monitor cardiorespiratory signals includes building a chamber from a silicone rubber, spin-coating a diaphragm from the silicone rubber, attaching the chamber to the diaphragm, inserting electrodes into the channel, filling the chamber with a liquid electrolyte solution; and sealing the chamber.

Also according to the disclosure, a system for monitoring cardiorespiratory signals includes a diaphragm including a chamber and a channel connected to the chamber, the diaphragm attached to a chest of a user and flexible to move with the chest. The system includes a plurality of electrodes including an anode and a cathode, the plurality of electrodes extending into the channel. The system includes a liquid electrolyte solution filling the chamber and the channel, the liquid electrolyte solution able to flow across the plurality of electrodes as mechano-acoustic movement of the chest moves the diaphragm. The system includes a voltage source configured to apply a voltage to the anode such that a reversable electrochemical current is detectable as an ionic flux from the anode to the cathode which is modulated when the liquid electrolyte solution flows across the plurality of electrodes. The system includes a controller for detecting the electrochemical currents and measuring cardiorespiratory signals from the electrochemical currents.

While embodiments of the invention have been described, it is not intended that these embodiments illustrate and describe all possible forms of the invention. Rather, the words used in the specification are words of description rather than limitation, and it is understood that various changes may be made without departing from the spirit and scope of the invention.

When introducing elements of various embodiments of the disclosed materials, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the disclosed materials have been described in detail in connection with only a limited number of embodiments, it should be readily understood that the embodiments are not limited to such disclosed embodiments. Rather, that disclosed can be modified to incorporate any number of variations, alterations, substitutions or equivalent arrangements not heretofore described, but which are commensurate with the spirit and scope of the disclosed materials. Additionally, while various embodiments have been described, it is to be understood that disclosed aspects may include only some of the described embodiments. Accordingly, that disclosed is not to be seen as limited by the foregoing description, but is only limited by the scope of the appended claims.

The invention claimed is:

1. A sensor for monitoring cardiorespiratory signals, comprising:
a diaphragm defining a surface of each of a chamber and a channel connected to the chamber;
a plurality of electrodes extending into the channel, the plurality of electrodes including at least a first anode and a first cathode; and
a liquid electrolyte solution that fills the chamber and flows into the channel, surrounding the plurality of electrodes;
wherein when a voltage is applied to the first anode, an electrochemical current is detectable as an ionic flux from the first anode to the first cathode when the liquid electrolyte solution modulates across the plurality of electrodes from mechano-acoustic movement of a chest.

2. The sensor of claim 1, wherein at least one of:
the chamber is circular and composed of a flexible rubber and the channel extends from a top of the chamber and is semi-circular in shape;
the diaphragm is composed of a silicone rubber; and
the chamber and the channel are disposed in a sensor body, and the diaphragm is attached to a top surface of the sensor body and covers the chamber and the channel.

3. The sensor of claim 1, wherein the electrochemical currents are measurable to determine cardiorespiratory signals.

4. The sensor of claim 3, further including a cavity;
wherein the cavity is positioned at a terminal end of the channel, opposite the chamber, and the cavity is void of the liquid electrolyte such that it provides volume for the liquid electrolyte solution.

5. The sensor of claim 1, wherein the plurality of electrodes includes a second cathode and a second anode.

6. The sensor of claim 5, wherein the plurality of electrodes are platinum and are fabricated on a silicon wafer covered with silicone dioxide.

7. The sensor of claim 5, wherein a distance of 10 μm is between each of the plurality of electrodes.

8. The sensor of claim 5, wherein the plurality of electrodes are made on a flexible polyimide material.

9. The sensor of claim 1, wherein the liquid electrolyte solution contains an iodide/triiodide redox couple.

10. The sensor of claim 1, wherein the liquid electrolyte solution contains a redox couple with an opposite redox reaction at the first anode and the first cathode.

11. A method of manufacturing the sensor of claim 1, comprising:
building the chamber and the channel from a silicone rubber;
spin-coating the diaphragm from the silicone rubber;
attaching the chamber and the channel to the diaphragm;
inserting the plurality of electrodes into the channel;
filling the chamber with the liquid electrolyte solution; and
sealing the chamber.

12. The method of claim 11, wherein building the chamber includes forming a chamber mold via a 3D printer.

13. The method of claim 12, wherein building the chamber includes pouring a silicone rubber mixture into the chamber mold, and curing the silicone rubber mixture.

14. The method of claim 13, further including degassing the silicone rubber mixture prior to curing the silicone rubber mixture.

15. The method of claim 11, wherein spin-coating the diaphragm includes rotating a silicone rubber film on an acrylic sheet.

16. A method of using a sensor to monitor cardiorespiratory signals, comprising:

placing a sensor with a diaphragm on a chest of a user such that the diaphragm faces towards the chest, wherein the diaphragm defines a surface of each of a chamber and a channel connected to the chamber;

applying a DC voltage to a plurality of electrodes extending into the channel; and detecting a mechano-acoustic signal by measuring two reversable electrochemical currents between the plurality of electrodes that are modulated by passing an electrolyte solution from the chamber to the channel as a result of mechano-acoustic movement of the chest.

17. The method of claim 16, further including moving a diaphragm of the sensor;

wherein movement of the diaphragm reflects mechano-acoustic movement of breathing and heartbeats of the user.

18. The method of claim 16, further including measuring cardiorespiratory signals from the reversable electrochemical currents.

19. The method of claim 16, wherein detecting the reversable electrochemical currents includes determining a triiodide flux from an anode to a cathode of the plurality of electrodes.

20. A system for monitoring cardiorespiratory signals, comprising:

a diaphragm defining a surface of each of a chamber and a channel connected to the chamber, the diaphragm adapted to be attached to a chest of a user and flexible to move with the chest;

a plurality of electrodes including an anode and a cathode, the plurality of electrodes extending into the channel;

a liquid electrolyte solution filling the chamber and the channel, the liquid electrolyte solution able to flow across the plurality of electrodes as mechano-acoustic movement of the chest moves the diaphragm;

a voltage source configured to apply a voltage to the anode such that a reversable electrochemical current is detectable as an ionic flux from the anode to the cathode when the liquid electrolyte solution modulates across the plurality of electrodes; and a controller for detecting the electrochemical currents and measuring cardiorespiratory signals from the electrochemical currents.

* * * * *